United States Patent [19]

Ash et al.

[11] 4,414,422

[45] Nov. 8, 1983

[54] PURIFICATION OF 4,4-DIHYDROXYBIPHENYL

[75] Inventors: Mary L. Ash; Timothy R. Diephouse; Robert M. Strom, all of Midland, Mich.

[73] Assignee: The Dow Chemical Company, Midland, Mich.

[21] Appl. No.: 376,867

[22] Filed: May 10, 1982

[51] Int. Cl.³ .............................................. C07C 37/70
[52] U.S. Cl. ..................................... 568/724; 568/753
[58] Field of Search ................................ 568/753, 724

[56] References Cited

U.S. PATENT DOCUMENTS

| | | | |
|---|---|---|---|
| 3,326,986 | 6/1967 | Dugan et al. | 568/724 |
| 3,919,330 | 11/1975 | Kwantes et al. | 568/724 |
| 3,972,950 | 8/1976 | Kwantes | 568/724 |
| 4,242,527 | 12/1980 | Mark et al. | 568/724 |
| 4,300,000 | 11/1981 | Reinitz | 568/724 |
| 4,320,234 | 3/1982 | Mark et al. | 568/724 |
| 4,340,768 | 7/1982 | Jinbo et al. | 568/730 |

FOREIGN PATENT DOCUMENTS

| | | | |
|---|---|---|---|
| 2758565 | 7/1978 | Fed. Rep. of Germany | 568/724 |
| 1538935 | 6/1968 | France | 568/724 |
| 38-13627 | 7/1963 | Japan | 568/724 |
| 946322 | 1/1964 | United Kingdom | 568/724 |

*Primary Examiner*—Werren B. Lone
*Attorney, Agent, or Firm*—Douglas N. Deline

[57] ABSTRACT

4,4'-Dihydroxybiphenyl is purified to remove sulfur-containing impurities, color bodies and/or phenyl-substituted phenol compounds by heating in the presence of a mixture of water and a water-miscible organic compound selected from acetone and $C_{1-6}$ alkanols or diols for a time sufficient to remove substantial quantities of the sulfur-containing impurity, color bodies and/or phenyl-substituted phenol compound and thereafter recovering the purified 4,4'-dihydroxybiphenyl.

8 Claims, No Drawings

PURIFICATION OF 4,4-DIHYDROXYBIPHENYL

BACKGROUND OF THE INVENTION

The purity of 4,4'-dihydroxybiphenyl is of extreme importance in order to prepare high quality polymeric products therefrom. In particular whether 4,4'-dihydroxybiphenyl is prepared by the oxidative coupling of 2,6-dialkylphenols followed by acid dealkylation of the 3,3',5,5'-tetraalkyl-4,4'-dihydroxybiphenyl product formed or by traditional sulfonation processes, several deleterious by-products may be present. Among these by-products may be sulfur-containing impurities that may be remnants of the acid dealkylation agent, reaction products thereof or products formed during the sulfonation process where such process is employed. Other contaminants may include color bodies and reaction by-products of the process, particularly phenyl-substituted phenols, such as para-phenylphenol. Some method of purification of 4,4'-dihydroxybiphenyl crude reaction product is always necessary.

In U.S. Pat. No. 4,242,527, a process is described for purifying diphenols such as bisphenol A comprising dispersing the crude p,p'-diphenol in a heated aqueous alcoholic or phenolic solution, so as to dissolve the p,p'-diphenol, separating insoluble residues and cooling the solution to reprecipitate the desired p,p'-diphenol product. However, when applied to crude mixtures of 4,4'-dihydroxybiphenyl, the above technique has proven ineffective due to the relative insolubility of 4,4'-dihydroxybiphenyl in aqueous systems even at elevated temperatures.

It is also known to contact the crude 4,4'-dihydroxybiphenyl in the sodium salt form with charcoal, activated carbon or other clarifying substance in aqueous solutions. The process is not preferred due to the added cost of the clarifying agent. In addition traditional processes such as washing with an organic solvent such as benzene, methylene chloride or toluene have proven ineffective to remove the sulfur-containing impurities peculiar to processes for preparing 4,4'-dihydroxybiphenyl.

SUMMARY OF THE INVENTION

According to the present invented process crude 4,4'-dihydroxybiphenyl may be purified by contacting the crude 4,4'-dihydroxybiphenyl with a system comprising water and a water-miscible organic compound selected from the group consisting of acetone and $C_{1-6}$ alkanols or diols for a time sufficient to dissolve impurities comprising p-phenylphenol and sulfur-containing compounds and thereafter recovering purified 4,4'-dihydroxybiphenyl.

DETAILED DESCRIPTION OF THE INVENTION

Suitable water-miscible organic compounds for use according to the present invented process include acetone, methanol, ethanol, n-propanol, isopropanol, n-butanol, sec-butanol, isobutanol, tertiary butanol, n-pentanol, n-hexanol, tertiary amyl alcohol, ethylene glycol, propylene glycol, diethylene glycol, etc. Preferred water-miscible organic compounds are methanol and acetone. The most preferred water-miscible organic compound is acetone.

According to one embodiment of the invention, crude 4,4'-dihydroxybiphenyl is dispersed in a mixture of water and the water-miscible organic compound and heated for a time sufficient to dissolve impurities. The undissolved 4,4'-dihydroxybiphenyl product is then removed by filtering, decanting or other means. Alternatively the slurry may be cooled prior to filtering or decanting. The latter method will reduce the amount of 4,4'-dihydroxybiphenyl carried over in the liquid. However, since 4,4'-dihydroxybiphenyl is at most only slightly soluble in the liquid medium, only slightly improved yields result by cooling the slurry prior to separation. Because small amounts of undesired impurities may also come out of solution upon cooling it is preferred in order to obtain the most highly pure product that separation be performed at an elevated temperature. Preferred temperatures are from about 40° C. to about the normal boiling point of the water-miscible organic compound. Where acetone or methanol are employed the preferred temperature is from about 40° C. to about 65° C.

It is understood that the purification process may be accomplished by first adding either one or the other of water or the water-miscible organic compound to the 4,4'-dihydroxybiphenyl before addition of the second component of the system.

The ratio of water to water-miscible organic compound may vary over wide limits from about 10:1 by volume to about 1:10 by volume. Preferred are solutions of about equal amounts by volume of each component.

Additional components may of course also be present in the system. For example, a small quantity of a basic compound such as an alkali metal hydroxide, carbonate, etc., may aid in neutralizing any remnant acid groups which may be present and aid in solubilizing such compound as well as the phenyl-substituted phenols. Additional organic compounds including water-miscible organic compounds may of course be present during the purification process. For example, a ternary mixture of water and two of the above-defined water-miscible organic compounds could be employed according to the invention.

It is advantageous to retain the slurry of crude 4,4'-dihydroxybiphenyl, water and water-miscible organic compound at an elevated temperature for a substantial time period prior to separation or removal of the 4,4'-dihydroxybiphenyl product. Suitable time periods are from about 1 hour to about 24 hours or more, and preferably from about 2 hours to about 16 hours. The exact time period will, of course, depend on the initial quantities of undesired by-products present and the desired purity of the purified product. The extended time periods are advantageously employed in order to remove substantially all of the undesired by-products. Shorter time periods tend to produce an inferior product. Therefore, it is seen that the above-described time periods are of critical importance to the success of the invention.

Because the desired product remains substantially insoluble throughout the purification process, removal of the undesired contaminants is rendered more difficult due to trapping of contaminants within the crystalline structure of the product. While elevated temperatures and pressures above the boiling point of the solvent system may be employed according to the invention in order to liquify the 4,4'-dihydroxybiphenyl thereby aiding in solubilizing the impurities, the relatively complicated and more expensive process equipment required by this later method weighs against the use of such elevated temperatures and pressures.

According to the invention, sulfur weight content of the purified 4,4'-dihydroxybiphenyl is preferably less than about 100 ppm and most preferably less than about 50 ppm. Phenyl phenolic by-products including p-phenylphenol, are preferably reduced to levels by weight of less than about 5000 ppm and preferably less than about 2000 ppm. Color bodies are additionally removed by the process to provide a final product of high purity and whiteness.

SPECIFIC EMBODIMENTS

Having described the invention, the following examples are provided as further illustrative and are not to be construed as limiting.

EXAMPLE 1

In a 250-ml flask fitted with a mechanical stirrer, reflux condenser and nitrogen inlet, was placed 50 g of crude 4,4'-dihydroxybiphenyl having a dark brown color and containing 1150 ppm (part per million by weight) sulfur. One hundred milliliters of a 50:50 (V:V) mixture of water and acetone were added. The resulting slurry was heated to 65° C. with stirring for 7 hours. The slurry was then cooled, filtered and washed with three 50-ml portions of the 50:50 acetone:water mixture. The filtered material was a white colored crystalline mass having sulfur content of less than 30 ppm. Yield was 95 percent.

EXAMPLE 2

The conditions of Example 1 were substantially repeated. The crude 4,4'-dihydroxybiphenyl was analyzed and found to contain 20000 ppm p-phenylphenol. After treatment as in Example 1 with a 50:50 mixture of acetone and water for 6 hours at 60° C., the filtered product was found to contain 3000 ppm p-phenylphenol.

EXAMPLE 3

To 10 g of 4,4'-dihydroxybiphenyl (sulfur content 520 ppm) was added 200 ml of methanol. The 4,4'-dihydroxybiphenyl was dissolved by gentle heating and then 50 ml of water was added to the solution. The resulting slurry was heated at reflux for about 16 hours. Methanol was then removed in vacuo and the solid precipitate recovered by filtration. The purified product had a sulfur content of 53 ppm. Yield was 97 percent.

EXAMPLE 4

In a 25-ml flask was placed crude 4,4'-dihydroxybiphenyl (5 g) containing about 1000 ppm sulfur impurity by weight. A mixture of ethylene glycol and water (10 ml) was added. The resulting slurry was heated to about 100° C. with stirring for 6 hours. The product was then filtered and washed with three 50-ml portions of water (25° C.). The product was air dried for about 16 hours. Analysis showed sulfur content by weight was 220±11 ppm.

What is claimed is:

1. A process for purifying crude 4,4'-dihydroxybiphenyl comprising contacting without substantially dissolving the crude 4,4'-dihydroxybiphenyl in a system comprising water and a water-miscible organic compound selected from the group consisting of acetone, and $C_{1-6}$ alkanols and diols at an elevated temperature and for a time sufficient to remove substantial quantities of phenyl-substituted phenols and sulfur-containing impurities and thereafter recovering the purified 4,4'-dihydroxybiphenyl.

2. A process according to claim 1 wherein the temperature is from about 40° C. to about the normal boiling point of the water-miscible organic compound.

3. A process according to claim 1 wherein the time is from about 1 hour to about 24 hours.

4. A process according to claim 3 wherein the time is from about 2 hours to about 16 hours.

5. A process according to claim 1 wherein the water-miscible organic compound is acetone or methanol.

6. A process according to claim 5 wherein the temperature is from about 40° C. to about 65° C.

7. A process according to claim 1 wherein the purified 4,4'-dihydroxybiphenyl contains less than about 100 ppm by weight sulfur and less than about 5000 ppm by weight phenyl-substituted phenol.

8. A process according to claim 7 wherein the purified 4,4'-dihydroxybiphenyl contains less than about 50 ppm by weight sulfur and less than about 2000 ppm by weight phenyl-substituted phenol.

* * * * *

UNITED STATES PATENT AND TRADEMARK OFFICE
CERTIFICATE OF CORRECTION

PATENT NO. : 4,414,422
DATED : November 8, 1983
INVENTOR(S) : Mary L. Ash, Timothy R. Diephouse & Robert M. Strom It is certified that error appears in the above—identified patent and that said Letters Patent is hereby corrected as shown below:

Title page, title "PURIFICATION OF 4,4-DIHYDROXYBIPHENYL" should read -- PURIFICATION OF 4,4'-DIHYDROXYBIPHENYL --.

Column 1, line 1, title "PURIFICATION OF 4,4-DIHYDROXY-BIPHENYL" should read -- PURIFICATION OF 4,4'-DIHYDROXY-BIPHENYL --.

Signed and Sealed this

Third Day of April 1984

[SEAL]

Attest:

Attesting Officer

GERALD J. MOSSINGHOFF

Commissioner of Patents and Trademarks